United States Patent [19]

Swope et al.

[11] Patent Number: 5,030,005

[45] Date of Patent: Jul. 9, 1991

[54] LIQUID CRYSTAL DEVICE FOR CALIBRATION AND TESTING OF OPTICAL INSTRUMENTS

[75] Inventors: Charles H. Swope, Raleigh; John G. Link; Douglas G. Haugen, both of Durham, all of N.C.

[73] Assignee: Akzo N.V., Arnhem, Netherlands

[21] Appl. No.: 442,604

[22] Filed: Nov. 29, 1989

[51] Int. Cl.$^5$ .................. G01J 1/02; G01D 18/00; G02F 1/13
[52] U.S. Cl. .................. 356/243; 250/252.1; 350/330
[58] Field of Search .............. 356/243, 335, 336, 337, 356/432, 436; 250/252.1, 331; 350/347 R, 347 V, 350 R, 330

[56] References Cited

U.S. PATENT DOCUMENTS 4,435,047 3/1985 Fergason .................. 350/350 R
4,595,292 6/1986 Amodeo et al. .............. 350/347 R Primary Examiner—Vincent P. McGraw
Assistant Examiner—LaCharles P. Keesee
Attorney, Agent, or Firm—Spencer & Frank

[57] ABSTRACT

A device and method for optical calibration of an optical instrument that measures optical characteristics along an optical path. A controllable shutter having electrically alterable optical characteristics is placed across the optical path of the instrument. An electrical control is connected to the shutter for selectively providing a variable voltage to the shutter to electrically alter optical characteristics of the shutter in a controlled manner so that the optical characteristics of the shutter correspond to selected optical characteristics.

10 Claims, 5 Drawing Sheets

FIG. 2
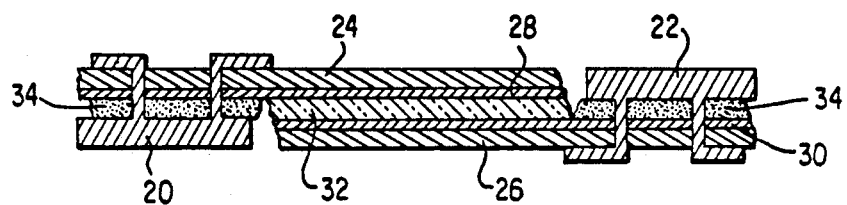
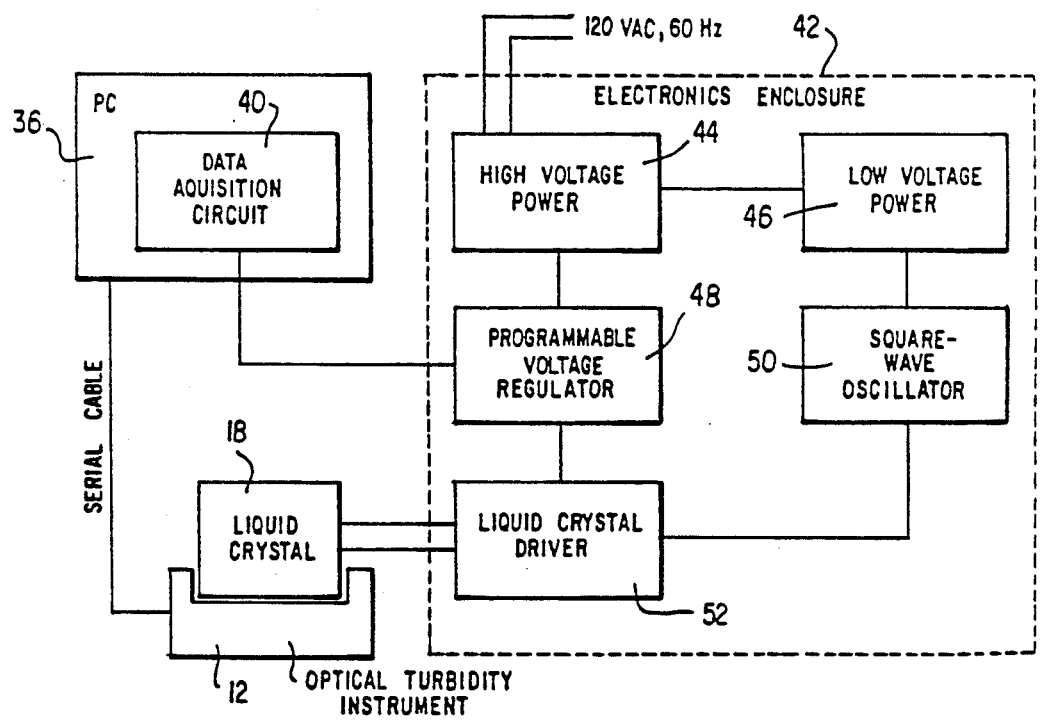
FIG. 6

LIQUID CRYSTAL DEVICE FOR CALIBRATION AND TESTING OF OPTICAL INSTRUMENTS

FIELD OF THE INVENTION

The present invention relates to a device for optical calibration of an optical instrument that measures optical characteristics, such as turbidity of a sample, and more specifically to a to device for simulating changes in light transmission and/or scattering to provide a simulated operating environment for the optical instrument.

TECHNOLOGY REVIEW

Instruments which analyze material based upon measurement of changes in optical properties of the material require both initial and periodic calibration and testing. A standard or reference reagent is necessary in order to adjust the instrument to provide a reading which represents a reference point. Procedures for calibration include the use of standard reagents having known values for the properties to be analyzed through the evaluation of the resultant optical properties.

For example, currently employed procedures for the testing of blood coagulation instruments include the use of standard reagents and standard blood samples. There are a number of inherent uncertainties associated with both standard blood samples and standard reagent preparation and handling requiring that a number of runs be performed in order to establish sufficient confidence in the results. In order to provide a standardized blood sample, blood from a large number of individuals is mixed to provide a statistically representative sample of a reliable average coagulation run. The procedure still must be performed and analyzed a number of times to ensure that the optical change is representative of the known mean value sought to be measured.

Even with this labor intensive and extensive testing, it is only possible to evaluate the optical analysis at one particular optical value, that of the statistical mean for the representative sample. These tests must be performed for a variety of separate blood coagulation situations, wherein different tests, such as PT, APTT, TT, and Fib, not only have different coagulation times but also produce different changes in levels of optical transmission between initial and final states of the reaction. In the case of instruments which analyze for a variety of optical levels, the standard sample test can leave an uncertainty in the optical regions not covered by the statistical samples.

SUMMARY OF THE INVENTION

It is an object of the invention to provide a consistent and reliable device for simulation of the optical properties of an analysis sample and to reduce the uncertainty and repetitive nature of sample analysis.

It is a further object of the present invention to eliminate the need to prepare actual samples for analysis in the testing of an optical instrument that measures turbidity.

It is another object of the present invention to provide a device for the evaluation of the optical response of an instrument over a broad range of optical transmission/scattering.

It is yet another object of the present invention to provide a device for generation of a smooth controlled transition between transmissive and scattering states in order to provide a clean optical simulation for testing for erratic instrument response.

The above and other objects are accomplished in accordance with the invention by the provision a device and method for optical calibration of an optical instrument that measures optical characteristics along an optical path. In accordance with the invention, a controllable shutter having electrically alterable optical characteristics is placed across the optical path of the instrument and a control mechanism is connected to the controllable shutter for selectively providing a variable voltage to the shutter to electrically alter optical characteristics of the shutter in a controlled manner so that the optical characteristics of the shutter correspond to selected optical characteristics.

Advantageously, the shutter is preferably shaped to fit into a sample receptacle of the optical instrument. Other advantageous features and details of the invention will become apparent from the description below when considered in conjunction with the drawings.

BRIEF DESCRIPTION OF THE DRAWINGS

FIG. 2 is a cross-sectional view of a liquid crystal shutter according the present invention.

FIG. 6 is a block circuit diagram showing the operational interaction of the shutter driver and the measuring instrument.

DESCRIPTION OF PREFERRED EMBODIMENTS

An embodiment of the present invention will be described with reference to coagulation testing of blood samples, it being understood that other applications of the invention are possible within the scope of the appended claims.

Figure 1:
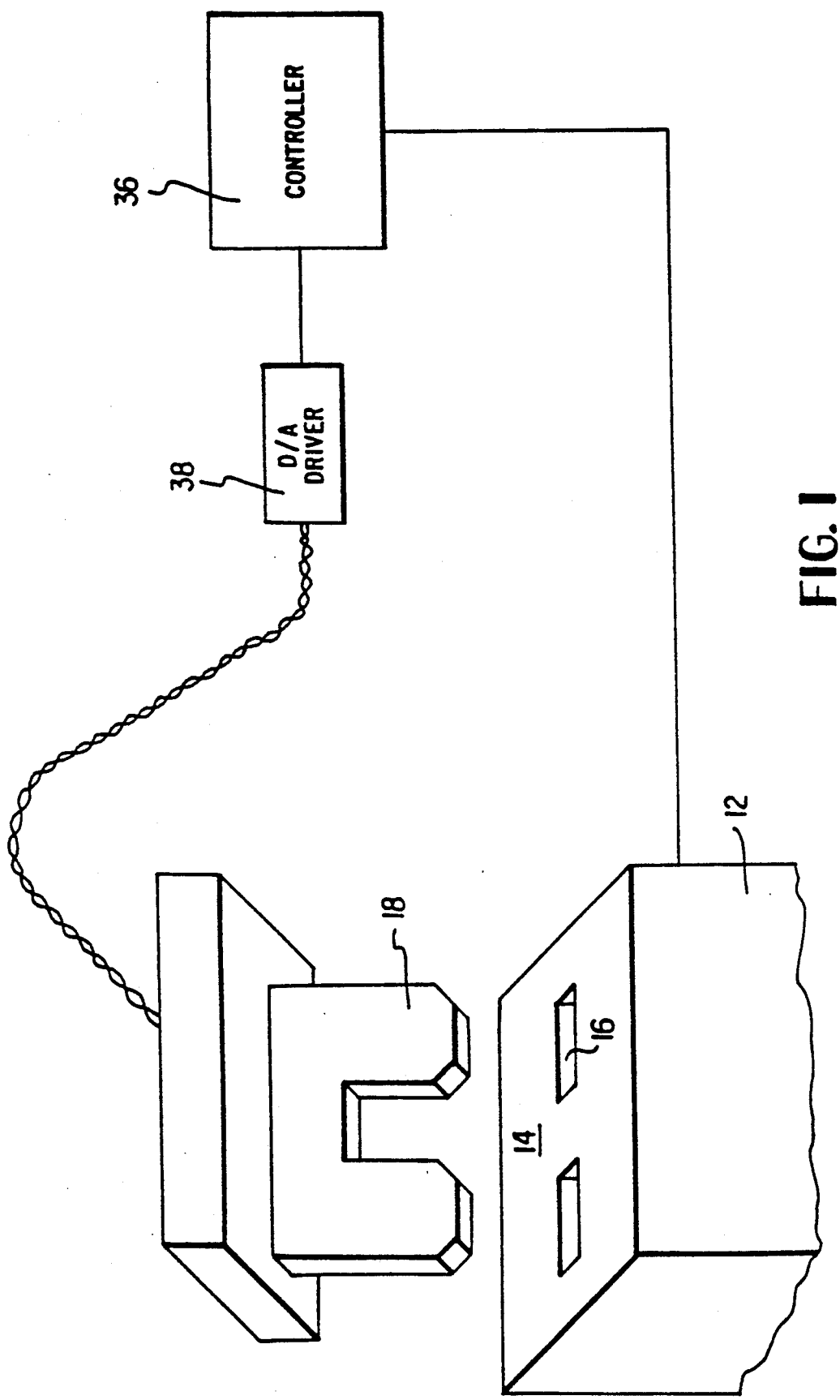
FIG. 1 is a perspective view showing a schematic representation of an optical instrument and controllable shutter according to an embodiment of the invention.

Referring to FIG. 1, there is shown a coagulation analysis device 12 having a light responsive sensor portion 14, which includes one or more light emitters and/or receivers (not shown). In normal operation a blood plasma sample is placed in a vial and liquid coagulation reagents are added. The vial is then placed in a slot 16 in sensor 14 and the blood allowed to coagulate. As the plasma sample coagulates, light scattered by the plasma sample increases and the sample becomes less transmissive. This optical change is detected by a properly functioning sensor, the details of which are known and form no part of the present invention.

In order to ensure that the sensor functions properly, it is necessary to test the sensor mechanism and to calibrate it if necessary. The sensor must detect with a degree of precision the time at which the sample crosses over the threshold of coagulation through detecting changes in its optical transmission. Therefore, it is necessary to provide the sensor with a optical stimulus which corresponds to the optical change in a sample. This can be done by providing an actual blood plasma sample with coagulation reagents. If the sample adequately represents the "average person's" plasma, then the measured coagulation time should approximate the statistical mean of coagulation times for the general population.

The present invention provides an alternative, more efficient technique for calibrating the sensor mechanism of an optical instrument. According to the invention, an optical stimulus simulating coagulation is provided by an optical element or shutter 18, which can be electrically controlled to exhibit optical characteristics which simulate changes in optical transmission of a standardized sample. Shutter 18 includes a liquid crystal having optical transmission characteristics which can be varied through the application of a selectively variable electrical voltage as will be described in greater detail below.

A controller 36, which can be a computer or similar operator interface mechanism, or an automated piece of hardware, sends a digital signal to a D/A converter and shutter driver 38, which supplies a corresponding voltage to the shutter 18. Controller 36 can be made to generate and send signals to simulate the desired optical characteristic. Typically a variety of simulations can be selected by the operator through controller 36.

As the simulation is run, the controller 36 receives data from instrument 12 indicative of the instrument's standard analysis of the optical characteristics of the simulation. These data are collected by controller 36 or by a separate instrument as desired.

Referring to FIG. 2, the shutter comprises a liquid crystal layer 32 sandwiched between transparent electrode layers 28 and 30 of indium tin oxide (a ceramic semiconductor comprised of $In_2O_3$ and $SnO_2$), which are in turn covered by transparent, Mylar-brand poly (ethylene terphthalate) layers 24 and 26. Terminals 20 and 22 form an electrical contact with electrode layers 28 and 30. Terminals 20 and 22 are connected to electrodes 28 and 30 by a silver epoxy 34 to prevent damage of the ceramic electrodes through heating and mechanical stress. Optionally, the shutter assembly shown in FIG. 2 may be enclosed in clear acrylic (not shown), or other suitable material, to allow for repeated insertion into optical slots 16 without undue stress on the liquid crystal film and/or layers. This encasement also shields the film from exposure to moisture which can alter the performance characteristics of the film. It is important to isolate the film and electrode layers from mechanical stress and from moisture since repeated use is almost certain to subject the shutter to both.

Liquid crystal layer 32 comprises a nematic liquid crystal as disclosed, for example, in U.S. Pat. No. 4,435,047. An optical shutter made with a nematic liquid crystal is disclosed in U.S. Pat. No. 4,556,289. A Low Haze Formula (LHF), nematic liquid crystal film for making an optical shutter is commercially available from the Taliq Corporation, Sunnyvale, Calif. as Varilite brand film. The construction of a liquid crystal device as shown in FIG. 2 is known and such a device, per se, does not form part of the present invention.

The liquid crystal film exhibits the spectral transmissive characteristics listed in tables I and II when powered by a square wave signal at 1 KHz of 10 volts and 0 volts, respectively:

TABLE I

| 10 Volts | |
|---|---|
| Wavelength (nm) | Transmission % |
| 350 | 1.8 |
| 400 | 19.9 |
| 500 | 50.0 |

TABLE I-continued

| 10 Volts | |
|---|---|
| Wavelength (nm) | Transmission % |
| 600 | 57.3 |
| 700 | 61.2 |

TABLE II

| 0 Volts | |
|---|---|
| Wavelength (nm) | Transmission % |
| 350 | 0.16 |
| 400 | 0.98 |
| 500 | 2.2 |
| 600 | 2.9 |
| 700 | 4.0 |

The dynamic range of variable transmission allows for a considerable degree of controlled optical simulation. This range, combined with the linearity of response which can be achieved if shutter 18 is properly driven, allows shutter 18 to be used for testing a variety of optical instruments that detect changes in light transmission in accordance with the principles of the invention.

Figure 5:
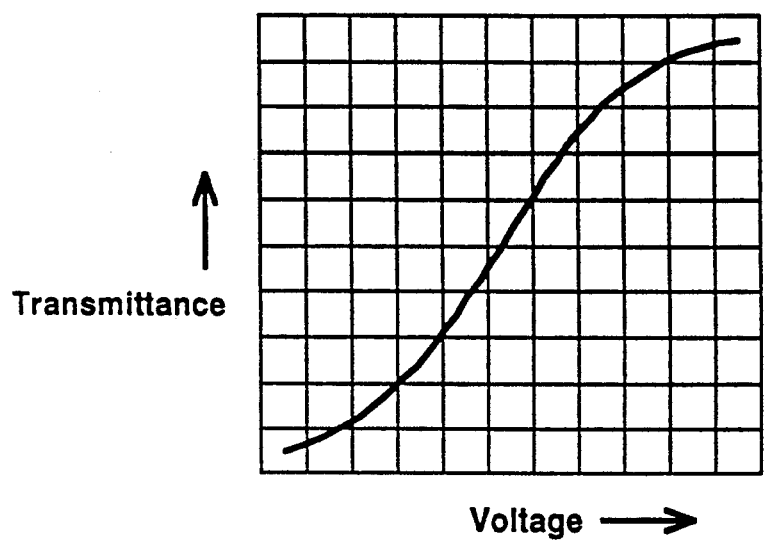
FIG. 5 is a graph illustrating the shutter transfer characteristics which illustrates the transmission characteristics of the shutter as a function of applied voltage.

The liquid crystal film utilized exhibits an optical response which is, by itself, not linear as a function of voltage amplitude. Therefore, in order to generate a reasonable simulation of the light transmission characteristics of the test sample being simulated, it is necessary to create a proportional voltage simulation characteristic. As illustrated in FIG. 5, there is a non-linear relationship between the voltage applied to the liquid crystal and its optical response characteristics.

The appropriate characteristic for the electrical drive signal applied to shutter 18 is derived through conditioning of the characteristic exhibited by the optical signal to be simulated. The conditioning comprises taking the characteristic of the desired optical signal to be simulated, such as Signal A, illustrated in FIG. 4, and through use of a mathematical algorithm arriving at an electrical signal characteristic for driving the liquid crystal to generate the desired simulated optical characteristic B.

In order to derive the appropriate voltage characteristics for the feed signal to produce the simulated optical characteristic B, the original waveform A is collected from the optical turbidity instrument 12 during a run of the instrument under standardized conditions. The waveform A must then be conditioned so that the electrical signal based on the conditioned waveform will drive the shutter 18 to produce characteristic B.

FIG. 5 illustrates the transmittance to voltage relationship for the shutter material. This curve is determined by placing a shutter 18 in the optical path of the sensor portion 14 of the analysis device 12, and then feeding a known voltage into the shutter 18 and correlating the detected transmittance. The known voltage is varied to determine the relationship across a voltage and transmittance range. The relationship between voltage and resultant transmittance is utilized in calculating a variable voltage drive signal to replicate the optical characteristic A.

To achieve the best fit, a tangent function modified by six additional power terms as shown for example below is used.

$$V = 25600 \{A \tan (Bx - C) + D + Ex + Fx^2 - Gx^3 + Hx^4 + Ix^5\}$$

where:
- V = voltage of drive signal
- X = measure of transmittance
- $A = 1.99351*10^{-2}$
- $B = 2.26815$
- $C = 5.90141$
- $D = 1.73714*10^2$
- $E = -3.39729*10^2$
- $F = 2.65441*10^2$
- $G = -1.03074*10^2$
- $H = 1.98986*10$
- $I = -1.52744$ The correlation between signal voltage and transmittance is then utilized to produce transmittance wave form B to simulate conditions for the optical turbidity instrument 12.

Distinct curves, such as characteristic A, can be collected for any number or variety of optical transmittance situations. The curves can be conditioned so that they can be simulated by driving shutter 18 with a voltage signal taking into account the voltage to transmittance ratio derived above.

The technique for learning and replicating the optical transmittance of a given event can thus be summarized as follows. First the event is performed, measured and repeated several times. Each of the measured transmittance characteristics is recorded, and they are collected together and evaluated to determine a standard transmittance curve. Once the standard transmittance curve is derived, an electrical signal is arrived at which will produce a replication of that transmittance curve by electrically driving an electrically controllable shutter. The value of the points along the standard transmittance curve are conditioned o converted into appropriate voltage values for driving the shutter to replicate the transmittance value points along the transmittance curve, as described above. It will be appreciated by those skilled in the art that any desired waveform (e.g. a square wave) may be conditioned in the above manner and used for calibration in accordance with the principles of the invention. The shutter is then driven with the voltage signal to replicate the standardized curve.

Further, the liquid crystal exhibits an imperfect amplitude response which is partly due to hysteresis of the liquid crystal. Therefore, it is desirable to utilize an overdrive algorithm in conjunction with the compensation algorithm to improve the simulation accuracy, in order to achieve the results illustrated by the characteristics in FIG. 4. The overdrive algorithm computes a running average ahead of the data point being manipulated, and alters the data point according to a fraction of the difference between it and the running average.

Figure 4:
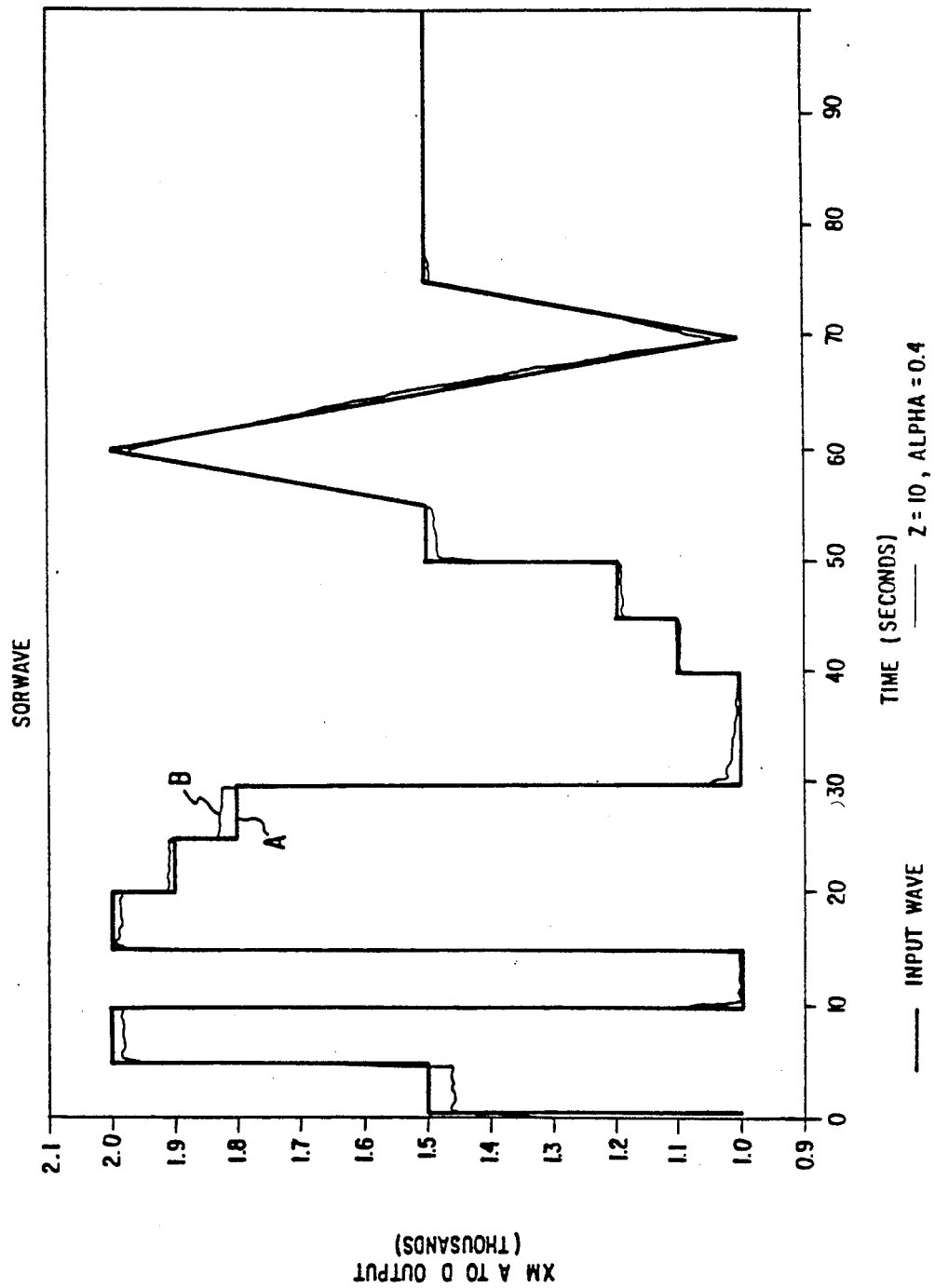
FIG. 4 is a graph representing the optical response of the liquid crystal shutter of the present invention.

Summarizing the foregoing, because the optical response of the film is not linear with respect to changes in voltage, a nonlinear voltage curve must be used to drive the shutter to replicate a given optical transmission characteristic to simulate a process for calibration. A curve fitting algorithm based on an inverse tangent function is used to adjust the voltage fed to the shutter to approximate the desired curve, combined with overdriving the shutter to compensate for the hysteresis and lag effects of the liquid crystal response. The results of this process are illustrated in FIG. 4, where the characteristic A represents the true waveform and characteristic B the shutter replication.

Figure 3:
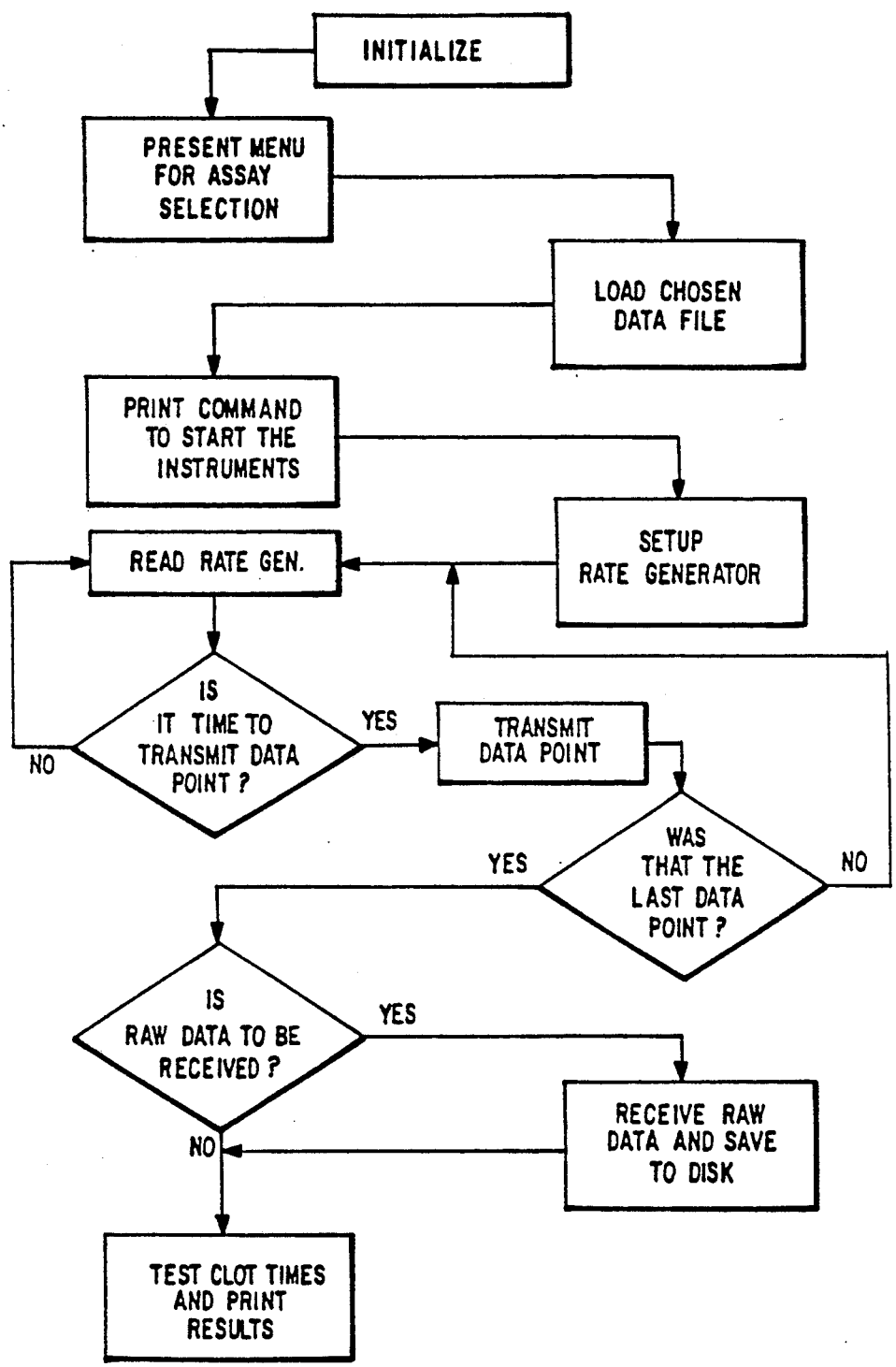
FIG. 3 is a logical flow diagram illustrating the test operation of the present invention.

FIG. 3 illustrates a logical flow diagram of the functional steps for simulation and evaluation of a test in the context of the system shown in FIG. 1. The system is first initialized and then a selection menu is presented to the operator to establish the appropriate settings on optical instrument 12 and to select the simulation to be run. The appropriate files are loaded and the operator is instructed to begin the analysis. Controller 36 then sends appropriate data to shutter 18 for the selected simulation, as the instrument 12 performs the appropriate evaluation on the simulated transmission. Either the raw transmission data or only the final resultant clotting times are retrieved by the controller as selected by the operator.

Controller 36 will then analyze the received data in either form and determine if the data are consistent with the expected results for the signals transmitted. The controller can be programmed to determine consistency within a given range in order to determine accuracy. Further, controller 36 can be utilized to evaluate the noise level in the received data to determine operational characteristics of the instrument. Since the optical signal from shutter 18 is smooth, the data should demonstrate a smooth response. A noisy response can indicate a deficiency in optical sensor 14 or associated circuitry of instrument 12. This analysis cannot be reliably performed with reagent sample calibration, because a reproducible smooth optical input cannot be assured.

It has been determined that for the purposes of optical testing the film is optimally driven by a square wave at a frequency of 1 KHz. At low driving frequencies the optical transmission characteristics are modulated and above 1 KHz the film can be damaged. It is also necessary to drive the film with a net zero DC waveform to avoid an electrical potential imbalance which will also damage the film.

FIG. 6 illustrates a block diagram of the control circuitry for driving the shutter and for receiving the data from the optical instrument in greater detail. The circuitry is comprised of three sections, the controller or computer 36, a data acquisition circuit 40 and a custom driver circuit 42. Data acquisition circuit 40 and custom driver circuit 42 comprise the generalized block 38 referred to as the D/A converter and driver of FIG. 1.

Data acquisition circuit 40 provides the appropriate timing for controlling the simulation rate. Circuit 40 also converts the digital signal from controller 36 to an analog voltage for driver circuit 42. Driver circuit 42, includes a power supply 44, low power converter 46, a variable voltage regulator 48, a square wave oscillator 50 and an output driver 52. The circuit provides the necessary controlled voltage to drive shutter 18 as described hereinabove.

The invention now being fully described, it will be apparent to one of ordinary skill in the art that many changes and modifications can be made thereto without departing from the spirit or scope of the invention as set forth herein. The specification is therefore to be viewed in an illustrative and not a limiting manner, the scope of the invention being defined by the following claims.

What is claimed is:

1. A device for optical calibration of an optical instrument that measures optical characteristics along an optical path, the device comprising:
   controllable shutter means having electrically alterable optical characteristics for placement across said optical path; and
   control means connected to said controllable shutter means for selectively providing a variable voltage to said shutter means to electrically alter optical characteristics of said shutter means in a controlled manner so that the optical characteristics of said shutter means correspond to selected optical characteristics.

2. The device set forth in claim 1, wherein the optical instrument measures turbidity with respect to time and said control means controls said shutter means to simulate optical characteristics representing changes in turbidity with respect to time of a predetermined standardized sample.

3. The device set forth in claim 1, wherein the optical characteristics altered by said control means include scattering.

4. The device set forth in claim 1, wherein the optical characteristics altered by said control means include transmission.

5. The device set forth in claim 1, wherein said control means provides a variable voltage to said shutter means to electrically alter optical characteristics of said shutter means for simulating the optical characteristics of clotting blood plasma.

6. The device set forth in claim 1, wherein the optical characteristics of said shutter means vary non-linearly with respect to changes of said voltage; and said control means provides a variable voltage according to a predetermined characteristic with respect to time which is selectively disproportionate to the non-linear change in the optical characteristic of said shutter means in order to achieve the desired optical response.

7. The device set forth in claim 1, wherein said shutter means is shaped to fit into a sample receptacle of said optical instrument.

8. A method for optical calibration of an optical instrument that measures changes in optical characteristics along an optical path, comprising:
   placing an optical shutter having electrically alterable optical characteristics across said optical path; and
   applying a variable voltage across the shutter for altering the optical characteristics of the shutter in a controlled manner so that the optical characteristics of the shutter correspond to selected optical characteristics.

9. The method set forth in claim 8, and further including shaping the shutter to fit into a sample receptacle of the optical instrument.

10. An optical calibration device for use with an optical instrument that measures optical characteristics of a sample along an optical path, the device comprising:
   controllable shutter means having electrically alterable optical characteristics, said shutter means being adapted for placement across said optical path in place of a sample; and
   control means connected to said shutter means for selectively outputting a variable voltage to electrically alter optical characteristics of said shutter means in a controlled manner so that the optical characteristics of said shutter means corresponds to desired optical characteristics for calibrating the optical instrument.

* * * * *